United States Patent [19]

Metzler

[11] Patent Number: Plant 7,003

[45] Date of Patent: Aug. 29, 1989

[54] PEACH TREE, "JEFFERSON SUN"

[75] Inventor: Ronald H. Metzler, Del Rey, Calif.

[73] Assignees: Metzler Investments; Metropolitan Life Insurance Company, both of Del Rey, Calif.

[21] Appl. No.: 258,875

[22] Filed: Oct. 17, 1988

[51] Int. Cl.[4] ..... A01H 5/00

[52] U.S. Cl. ..... Plt./43

[58] Field of Search ..... Plt./43

*Primary Examiner*—Robert E. Bagwill

*Attorney, Agent, or Firm*—Worrel & Worrel

[57] ABSTRACT

A new and distinct variety of peach tree which is somewhat remotely similar to the Berenda Sun Peach Tree (U.S. Plant Pat. No. 5,297) with which it is most closely related but from which it is distinguished therefrom by producing fruit which are mature for harvesting and shipment approximately three to four weeks prior to the fruit produced by the Berenda Sun Peach Tree and which further produce a globose shaped fruit which is freestone by nature and which further exhibits a deep red to lighter yellow skin color and a light yellow colored flesh.

1 Drawing Sheet

BACKGROUND OF THE NEW VARIETY

The present invention relates to a new and distinct variety of peach tree which will hereinafter be denominated varietally as "Jefferson Sun" and more particularly to such a peach tree which produces fruit which are mature for commercial harvesting and shipment during the last week of June through as late as July 5 in the San Joaquin Valley, of Central California; and which further is distinguished principally as to novelty by producing a freestone fruit, the flesh of which is very firm and crisp and has a clear yellow color, and which further has a pleasing globose shape, the fruit of the subject variety further having noteworthy shipping and handling characteristics.

The applicant has endeavored throughout his professional career to develop new and novel varieties of fruit trees. The new and novel variety of peach tree hereof was discovered in the summer of 1981 during routine orchard operations, as a sport branch growing on a Berenda Sun Peach Tree (U.S. Plant Pat. No. 5,297). The fruit produced by the sport branch were noted at that time to have a novel color and a harvesting date which appeared somewhat different from the remainder of the fruit growing on the tree.

It has long been known that the purchase of fruits, such as peaches by consumers may be influenced to some extent by the fruit's exterior appearance. For example, the purchase may be influenced by the size, a pleasing shape, and a noteworthy skin coloration. Further, such other characteristics as the crisp nature of the flesh, and a skin is tenacious to the flesh may permit the variety to achieve wide commercial acceptance inasmuch as it may handle and store quite well thereby permitting it to be transported to distant markets.

Thus, it has long been recognized that it would be desirable to provide a peach tree which produces fruit which are ripe for commercial harvesting and shipment during the last week of June or early July and which further have a commercially aesthetic appeal such as that presented by the Berenda Sun Peach Tree (U.S. Plant Pat. No. 5,297), but which is distinguished therefrom, and characterized principally as to novelty, by having a date of harvesting and shipment which is approximately three to four weeks earlier than that of the Berenda Sun Peach Tree (U.S. Plant Pat. No. 5,297).

ORIGIN AND ASEXUAL REPRODUCTION OF THE NEW VARIETY

The present variety of peach tree hereof was discovered by the inventor on Ranch Number 60 of the applicant's employer, the H. P. Metzler & Sons Company of De Rey, Calif. The new and novel variety was discovered as a sport branch growing on a Berenda Sun Peach Tree (U.S. Plant Pat. No. 5,297), the subject tree growing within the cultivated area of Ranch Number 60 which is located near 5286 South Del Rey Ave., in Del Rey, Calif. The discovery, which occurred during the summer of 1981, was noted at that time, to produce fruit which had a noteworthy skin color and a harvesting date which appeared somewhat earlier than the remainder of the fruit produced by the same tree. The inventor marked the sport branch for subsequent observation. In the following year, the applicant observed that the sport branch produced the same type of fruit which had been observed during the summer of 1981. The applicant, thereafter, removed bud wood during the winter of 1982 and 1983 and budded it into test trees which were located within the H. P. Metzler & Sons test block at Del Rey, Calif. This first asexual reproduction produced fruit in 1984. The fruit and the trees were again observed in 1985. It has subsequently been determined that this first asexual reproduction dependably and accurately reproduced the superior characteristics observed by the applicant in the original sport limb.

SUMMARY OF THE NEW VARIETY

The Jefferson Sun Peach Tree is characterized as to novelty by producing fruit which have an appealing shape and a highly attractive skin color. Further, the fruit of the Jefferson Sun Peach Tree is ripe for commercial harvesting and shipment from approximately the last week in June to as late as July 5 in the San Joaquin Valley of central California. The new and novel variety is most closely similar to the Berenda Sun Peach tree (U.S. Plant Pat. No. 5,297) from which it was derived as a sport limb, but which is distinguishable therefrom and characterized principally as to novelty by producing fruit which have a noteworthy skin color and a pleasing round shape and which further are ripe for commercial harvesting and shipment approximately three to four weeks earlier than the fruit produced by the Berenda Sun peach tree. Morover, the fruit of the subject variety handles well during harvesting and packing and has excellent cold storage characteristics.

BRIEF DESCRIPTION OF THE DRAWINGS

The drawing is a color photograph of several mature fruit characteristic of the subject variety. The several fruit shown in the photograph display the skin colorations typical of the fruit which are sufficiently matured for commercial harvesting and shipment. Another cross-sectioned fruit is shown in the photograph displaying the flesh coloration on a typically mature fruit. The photograph also shows a typical twig bearing characteristic leaves which display the top and bottom surface colors thereof, together with a typical stone all of the instant variety.

DETAILED DESCRIPTION

Referring more specifically to the pomological details of this new and distinct variety of peach tree, the following characteristics were observed under the ecological conditions prevailing at the orchard of origin which is located at 5286 South Del Rey Ave., in Del Rey, Calif. All major color code designations are by reference to the Inter-Society Color Council, National Bureau of Standards. Common color names are also used occasionally.

Tree:

*Size.*—Generally — Normal as compared with other peach cultivars.

*Vigor.*—Very vigorous.

*Form.*—Average as compared with other peach tree varieties. The ultimate form of the instant variety is determined by pruning practices.

*Productivity.*—Considered very good as compared with other peach tree varieties.

*Regularity of bearing.*—Regular. The subject variety has produced a good crop during the last several years it was observed.

Trunk:

*Size.*—Average.

*Surface texture.*—Average. The variety displays characteristically rough peach tree bark.

*Color.*—Surface Texture — Brown, (61. gy. Br.).

*Lenticels.*—Numbers — Approximately 18 lenticels per square inch were found.

Branches:

*Size.*—Average.

*Surface texture.*—The surface texture of the bark is considered average and is substantially identical to the surface texture of the trunk.

*Color.*—Surface texture — Brown, (61. gy. Br.).

*Lenticels.*—Numbers — Approximately eighteen lenticels per square inch were found.

Leaves:

*Size.*—Generally — Average.

*Average length.*—Approximately six to seven inches, (152.4–177.8 mm.).

*Average width.*—Approximately $1\frac{5}{8}$ inches, (41.27 mm.).

*Marginal form.*—Generally — Serrate.

*Leaf base — Form — Acute.*

*Surface texture.*—Glabrous, and appearing almost waxy.

*Shape.*—Generally — Lanceolate.

*Color.*—Upwardly disposed surface — Green, (126. d. O1 G). Downwardly disposed surface — Pale green, (125. m. O1 G).

*Petiole.*—Average length — Approximately 7/16" (11.11 mm.). Average width — Approximately 1/16" (1.58 mm.) Color — Green, the color of the petiole is not particularly distinctive of the subject variety.

*Stem glands.*—Numbers — Two. Arrangement — The two stem glands are opposite and appear at the base of the leaf. Size — The stem glands are generally considered to be small. Form — Reniform. Color — Yellowish-green, (99. s. g Y.).

Flower buds:

*Generally.*—The flower bud characteristics of the subject variety were osberved when the first red appeared at the apex of the bud. The flower buds are considered to be average as compared with the other peach cultivars.

*Shape.*—Generally — Slightly elongated.

*Size.*—Average Diameter — Approximately 7/32", (5.55 mm.). Average Length — Approximately 5/16", (7.938 mm.).

*Color.*—Grayish-red (23. d. r Gray).

Flowers:

*Date of bloom.*—Variable. The subject variety may bloom during the last week of February to as late as March 4 at Del Rey, Calif.

*Petals.*—Shape — Slightly elongated. Average Width — Approximately 3/8", (9.25 mm.). Average Length — Approximately 9/16", (14.28 mm).

*Color.— Dark pink,* (250. m. p Pk.).

*Size.*—Generally — The flowers of the subject variety are average as compared to the flowers produced by other peach cultivars.

Fruit:

*Maturity when described.*—Ripe for commercial harvesting and shipment during the fourth week of June through approximately July 5 in Del Rey, Calif.

*Uniformity.*—Average.

*Average axial diameter.*—Variable, approximately $2\frac{3}{4}$" to $3\frac{1}{2}$", (69.85 mm.–88.9 mm.).

*Average diameter in the suture plane.*—Approximately $2\frac{3}{4}$" to $3\frac{1}{2}$", (69.85 mm.–88.9 mm.).

*Average diameter transverse in the suture plane.*—Approximately $2\frac{3}{4}$" to $3\frac{1}{2}$", (69.85 mm.–89.9 mm.).

*Average diameter transverse and at right angles to the suture plane.*—$2\frac{3}{4}$" to $3\frac{1}{2}$", (69.85 mm.–88.9 mm.).

*Form.*—Uniformity — Good. Symmetry — Symmetrical. Suture — The suture appears as a smooth yet distinct line which extends from the base to the apex. Further, the suture appears to hold up quite well. More particularly, the fruit of the subject variety, which were examined, showed no evidence of breaking down along or about the suture line.

*Suture.*—Length — Approximately $3\frac{1}{4}$" to $3\frac{1}{2}$", (82.55–88.9 mm.).

*Ventral surface.*—Shape — Rounded and may occasionally appear slightly flat.

*Stem cavity.*—Depth — Approximately $\frac{3}{8}$", (9.52 mm.). Shape — Rounded.

*Base.*—Shape — Average in width and may from time to time appear flat.

*Apex.*—Shape — Slightly rounded and occasionally appearing almost flat.

*Pistil point.*—Shape — Very small and appearing almost receded.

*Stem.*—Average length — Approximately $\frac{3}{8}''$, (9.52 mm.). Average thickness — Approximately 3/16", (4.76 mm.).

*Skin.*—Thickness — Average as compared with the skin of other peach cultivars. Strength — Generally considered strong.

*Tenacious to flesh.*—Yes.

*Tendency to crack.*—Not observed.

*Skin color.*—Dark red and having some yellow shading. The color red is variable, (14. v. deep Red through 16. d. Red; and 86. 1 Y).

*Pubescence.*—Present, although it is considered light.

*Flesh color.*—Light yellow, (86. 1 Y).

*Texture of pit cavity.*—Considered rough.

*Pit cavity.*—Color — Dark Red, (13. deep. Red).

*Flavor.*—Mild and slightly acidic.

*Aroma.*—Slight.

*Fibers.*—Not present. The flesh has a very smooth texture.

*Ripening.*—Considered even.

*Overall eating quality.*—Crisp and having a noteworthy flavor.

Stone:

*Attachment.*—Freestone.

*Fibers.*—No fibers are evident.

*Size.*—Average Length — Approximately $1\frac{5}{8}''$, (41.27 mm.). Average width — Approximately 1", (25.4 mm.). Average thickness — Approximately $\frac{3}{4}''$, (19.05 mm.).

*Form.*—Ovid.

*Base.*—Form — Small and flat.

*Apex.*—Form — Considered long, approximately 3/16", (4.76 mm.).

*Sides.*—Surface Texture — Very rough.

*Ridges.*—Pattern — Considered mixed. Height — Approximately $\frac{1}{8}''$, (3.17 mm.). Color — Brownish-red, (43. m. r Br).

*Tendency to split.*—Not observed.

Fruit use: Fresh market peach for use in both local and long distance markets.

Keeping quality: Noteworthy. The variety has been kept in cold storage in excess of three weeks with no deleterious effects noted.

Shipping and handling quality: Exceptional. The crisp nature of the flesh in combination with the tenacious skin characteristics indicates that the instant variety of peach tree will have noteworthy shipping and handling characteristics.

Although the new variety of peach tree possesses the described characteristics noted above as a result of the growing conditions prevailing in Del Rey, Calif., in the central part of the San Joaquin Valley of central California, it is to be understood that variations of the usual magnitude and characteristics incident to changes in growing conditions, fertilization, pruning and pest control are to be expected.

Having thus described and illustrated my new variety of peach tree, what I claim as new and desire to be secured by Plant Letters Patent is:

1. A new and distinct variety of peach tree substantially as illustrated and described and which is somewhat remotely similar to the Berenda Sun Peach Tree (U.S. Plant Pat. No. 5,297) from which it was derived as a chance sport but from which it is distinguished therefrom and characterized principally as to novelty by producing fruit which are mature for commercial harvesting and shipment during the last week of June through July 5 in the San Joaquin Valley of central California and which further produces a freestone fruit which has a red and yellow skin color and a flesh color which is a pleasing light yellow, the fruit of the subject variety having noteworthy shipping and handling characteristics.

* * * * *

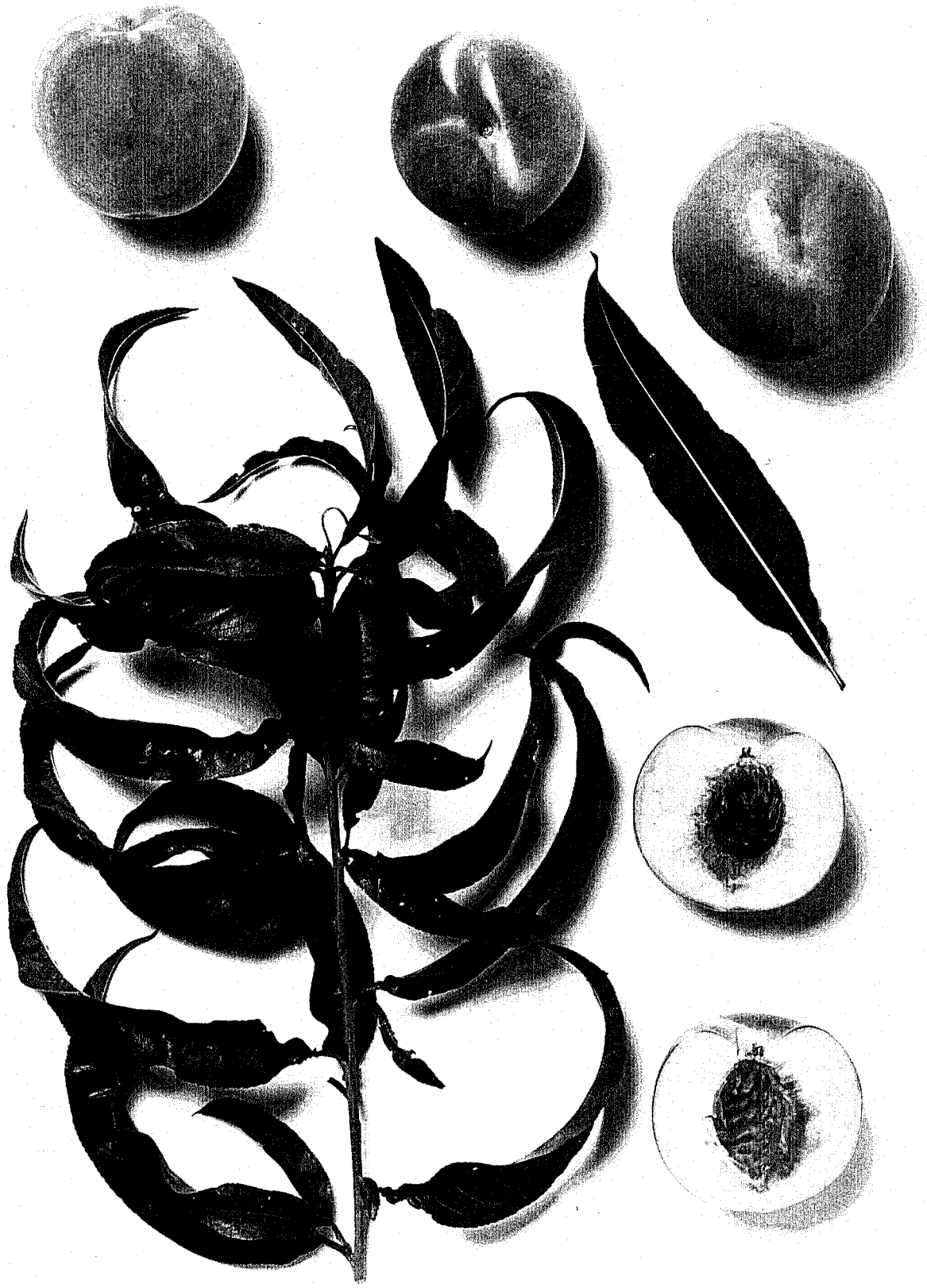

UNITED STATES PATENT AND TRADEMARK OFFICE

CERTIFICATE OF CORRECTION

PATENT NO. : PP 7,003

DATED : August 29, 1989

INVENTOR(S) : Ronald H. Metzler

It is certified that error appears in the above-identified patent and that said Letters Patent is hereby corrected as shown below:

Column 2, Line 9

Delete "De"
Insert ---Del---

Column 3, Line 15

Delete "on"
Insert ---of---

Signed and Sealed this

Twentieth Day of March, 1990

*Attest:*

*Attesting Officer*

JEFFREY M. SAMUELS

*Acting Commissioner of Patents and Trademarks*